(12) United States Patent
Winniford et al.

(10) Patent No.: US 8,318,896 B2
(45) Date of Patent: Nov. 27, 2012

(54) CHROMATOGRAPHY OF POLYOLEFIN POLYMERS

(75) Inventors: William L. Winniford, Lake Jackson, TX (US); Rongjuan Cong, Lake Jackson, TX (US); Theodore M. Stokich, Jr., Midland, MI (US); Randy J. Pell, Midland, MI (US); Matthew D. Miller, Lake Jackson, TX (US); Abhishek Roy, Edina, MN (US); Freddy Van Damme, Brugge (BE); Alexander W. Degroot, Sugar Land, TX (US); John W. Lyons, Midland, MI (US); David M. Meunier, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 12/643,111

(22) Filed: Dec. 21, 2009

(65) Prior Publication Data

US 2011/0152499 A1 Jun. 23, 2011

(51) Int. Cl.
*C08F 6/00* (2006.01)
*C08G 64/00* (2006.01)

(52) U.S. Cl. ........ 528/502; 210/101; 210/143; 210/149; 210/198.2; 210/656; 506/12

(58) Field of Classification Search ................. 210/101, 210/143, 149, 198.2, 656; 506/12; 528/502
See application file for complete search history.

(56) References Cited

U.S. PATENT DOCUMENTS

| | | | |
|---|---|---|---|
| 5,272,236 A | 12/1993 | Lai et al. | |
| 5,278,272 A | 1/1994 | Lai et al. | |
| 6,260,407 B1 | 7/2001 | Petro et al. | |
| 6,406,632 B1 | 6/2002 | Safir et al. | |
| 6,730,228 B2* | 5/2004 | Petro et al. | 506/12 |
| 6,855,258 B2* | 2/2005 | Petro et al. | 506/12 |
| 7,214,320 B1* | 5/2007 | Gregori et al. | 210/656 |
| 7,355,089 B2 | 4/2008 | Chang et al. | |
| 8,076,147 B2 | 12/2011 | Van Damme et al. | |
| 2002/0056686 A1* | 5/2002 | Kyrlidis et al. | 210/656 |

FOREIGN PATENT DOCUMENTS

| | | |
|---|---|---|
| WO | WO2006/081116 | 8/2006 |
| WO | WO2006/127717 | 11/2006 |

OTHER PUBLICATIONS

Stoll, Dwight R.; Li, Xiaoping; Wang, Xiaoli; Carr, Peter W.; Porter, Sarah E. G.; Rutan, Sarah C. Fast, comprehensive two-dimensional liquid chromatography. Journal of Chromatography, A (2007), 1168(1-2), 3-43. CODEN: JCRAEY ISSN:0021-9673. CAN 148-26573 AN 2007:1139459 CAPLUS.

Schoenmakers, Peter J.; Vivo-Truyols, Gabriel; Decrop, Wim M. C. A protocol for designing comprehensive two-dimensional liquid chromatography separation systems. Journal of Chromatography, A (2006), 1120(1-2), 282-290. CODEN: JCRAEY ISSN:0021-9673. CAN 145:240469 AN 2006:609970 CAPLUS.

Wang Xiaoli; Stoll Dwight R; Carr Peter W; Schoenmakers Peter J A graphical method for understanding the kinetics of peak capacity production in gradient elution liquid chromatography. Journal of chromatography. A (2006), 1125(2), 177-81. Journal code: 9318488. ISSN:0021-9673. PubMed ID 16777118 AN 2006481124 MEDLINE.

Stokich, Theodore M., Jr.; Meunier, David M.; DeGroot, A. Willem; Edam, Rob. 2-D molecular topology fractionation (MTF) X size-exclusion chromatography (SEC) system development and application to branched polyethylene polymers. Abstracts of Papers, 236th ACS National Meeting, Philadelphia, PA, United States, Aug. 17-21, 2008, ANYL-251. CODEN: 69KXQ2 AN 2008:949472 CAPLUS.

Edam, R.; Meunier, D. M.; Mes, E. P. C.; Van Damme, F. A.; Schoenmakers, P. J. Branched-polymer separations using comprehensive two-dimensional molecular-topology fractionation. times. size-exclusion chromatography. Journal of Chromatography, A (2008), 1201(2), 208-214. CODEN: JCRAEY ISSN:0021-9673. CAN 149:356438 AN 2008:905715 CAPLUS.

Meunier, David M.; Stokich, Theodore M.; Edam, Rob; Schoenmakers, Peter J.; Gillespie, David; deGroot, A. Willem. Characterization of long chain branched polymers by 2-D molecular topology fractionation X size-exclusion chromatography. Abstracts of Papers, 235th ACS National Meeting, New Orleans, LA, United States, Apr. 6-10, 2008, POLY-370. CODEN: 69KNN3 AN 2008:392533 CAPLUS.

Meunier, David M.; Stokich, Theodore M., Jr.; Edam, Rob; Schoenmakers, Peter J.; Gillespie, David; deGroor, Willem. Two dimensional molecular topology fractionation X size-exclusion chromatography for characterization of long chain branched polymers. Polymer Preprints (American Chemical Society, Division of Polymer Chemistry) (2008), 49(1), 131-132. CODEN: ACPPAY ISSN:0032-3934. CAN 150:214956 AN 2008:368298 CAPLUS.

Meunier, David M.; Stokich, Theodore M., Jr.; Gillespie, David; Smith, Patrick B. Molecular topology fractionation of polystyrene stars and long chain branched polyethylene fractions. Macromolecular Symposia (2007), 257(Polyolefin Characterization), 56-70. CODEN: MSYMEC ISSN:1022-1360. CAN 148:145266 AN 2007:1373832 CAPLUS.

Albrecht, et al. Macromolecules, 2007, 40, 5545.
Albrecht, et al. Macromol. Symp. 2007, 257, 46.
Chitta, et al. J. of Chromatography A. 1217 (2010) 7717-7722.
Chaimbault, et al., J. of Chromatography A., 797, (1998), 83-91.
Christian-Heinz et al, Polymer, 46, (2005), 12040-12045.
Findenegg, et al. Carbon, vol. 25, No. 1 (1987), 119-128.

(Continued)

*Primary Examiner* — Terressa Boykin

(57) ABSTRACT

A method for multi-dimensional chromatography of a polyolefin polymer, comprising introducing a solution of the polyolefin polymer into a liquid flowing through a first liquid chromatography stationary phase or a field flow fractionation device and subsequently flowing the solution through a second liquid chromatography stationary phase, the second liquid chromatography stationary phase comprising graphitic carbon, the polyolefin polymer emerging from the liquid chromatography stationary phase with a retention factor greater than zero.

15 Claims, 4 Drawing Sheets

OTHER PUBLICATIONS

Hanai, J. of Chromatography A, 989, (2003), 183-196.
Ginzburg, et al. J. of Chromatography A. 1217 (2010) 6867-6874.
Im K, et al. J. of Chromatography vol. 1216, No. 21, 2009, 4606-4610.
Leboda, et al. Materials Chemistry and Physics 55 (1998) 1-29.
Macko, et al. J. Chrom. A, 1002 (2003) 55-62.
Macko, et al. J. Chrom. A, 1115 (2006) 81-87.
Macko, et al. Polymer 50 (2009), 5443-5448.
Macko, et al. Macromolecules (2009) 42, 6063-6067.
Macko, et al. Macromolecular Symposia, vol. 298 (2011) 182-190.
Macko, et al. J. Sep. Sci., vol. 26, (2003), 1569-1574.
Macko, et al. J. Sep. Sci., vol. 28, (2005), 59-64.
Macko, et al. Chromatographia, vol. 64, No. 3-4, (2006), 183-190.
Marin, et al. J. of Chromatography, vol. 1030, No. 1-2, (2004), 255-262.
Mockel, et al. J. of Liquid Chromatography, vol. 14 (13), (1991), 2477-2498.
Pasch, et al. Pure and Applied Chem., vol. 80, No. 8, (2008), 1747-1762.
Pereira, et al. J. of Separation Sci., vol. 30, No. 8, (2007), 1115-1124.
Roy, et al. Macromolecules (2010) 43, 3710-3720.
Wang, et al. Macromolecules, vol. 38, No. 25, (2005) 10341-10345.

* cited by examiner

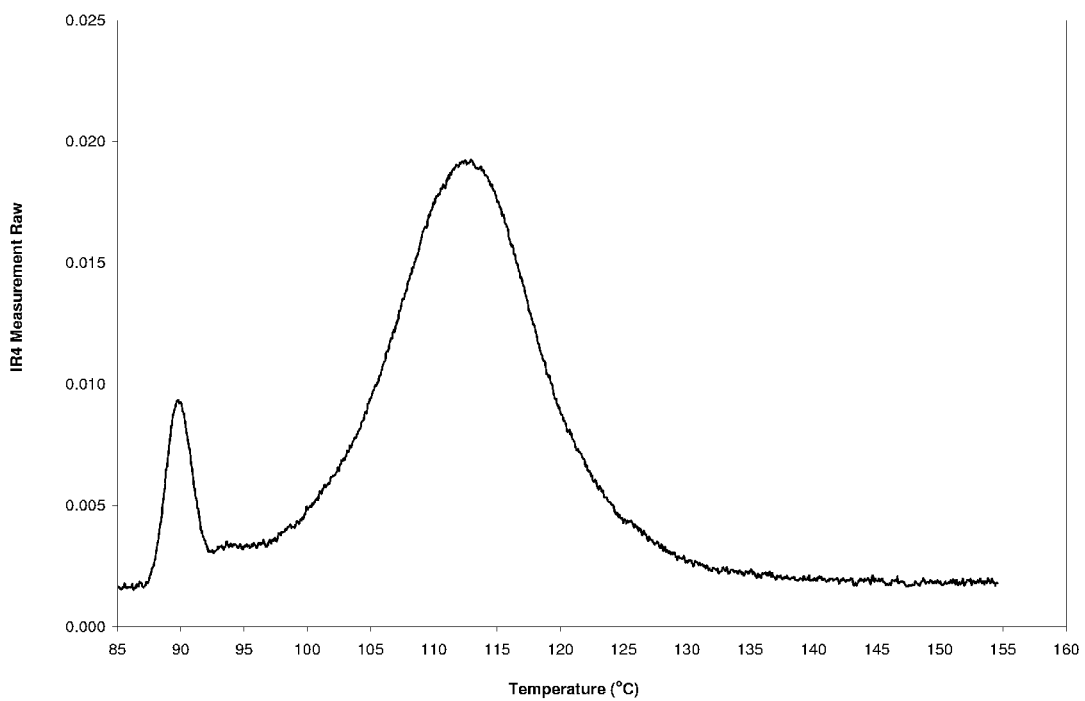
Figure 1a. TGIC chromatogram of a metallocene polymerized ethylene-octene polymer.

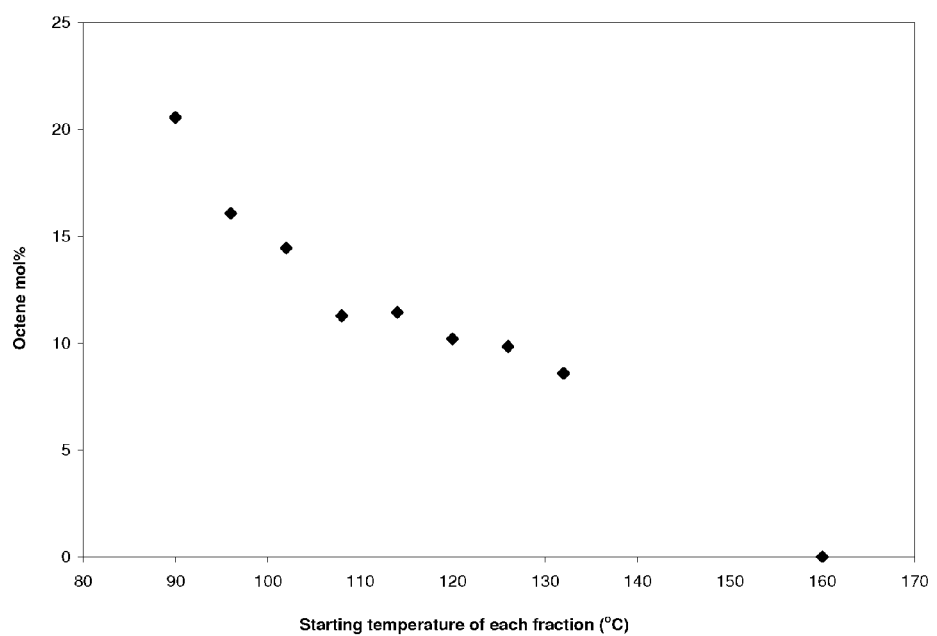
Figure 1b. Octene mol% in the fraction collected from TGIC of a metallocene polymerized ethylene-octene polymer.

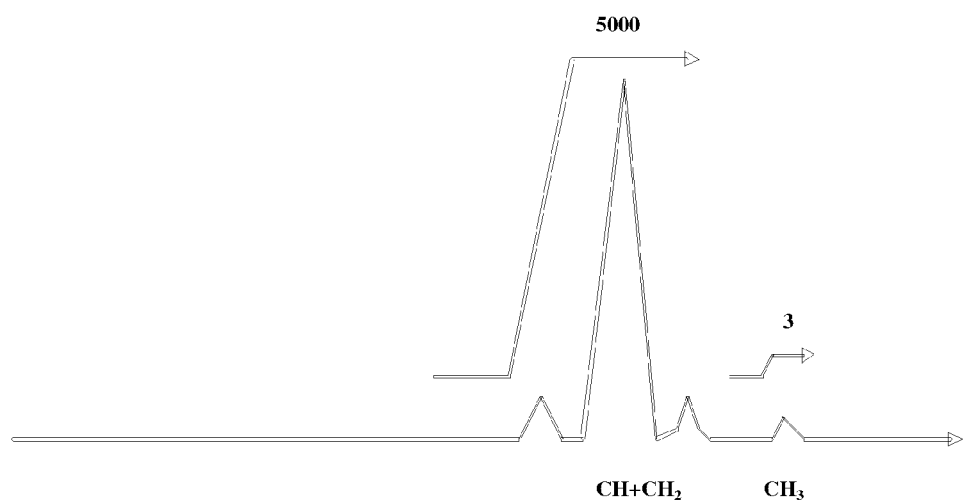
An example EO: Octene (Oct) (relative mole)=3/3=1
Ethylene (Eth) (relative mole)=(5000-13*1)/4=1246.8
Octene mol%=100*Oct(relative mole)/(Oct(relative mole)+Eth(relative mole))
Figure 2. Calculation of octene mol% from 1H NMR by assuming the end group effect being negligible.

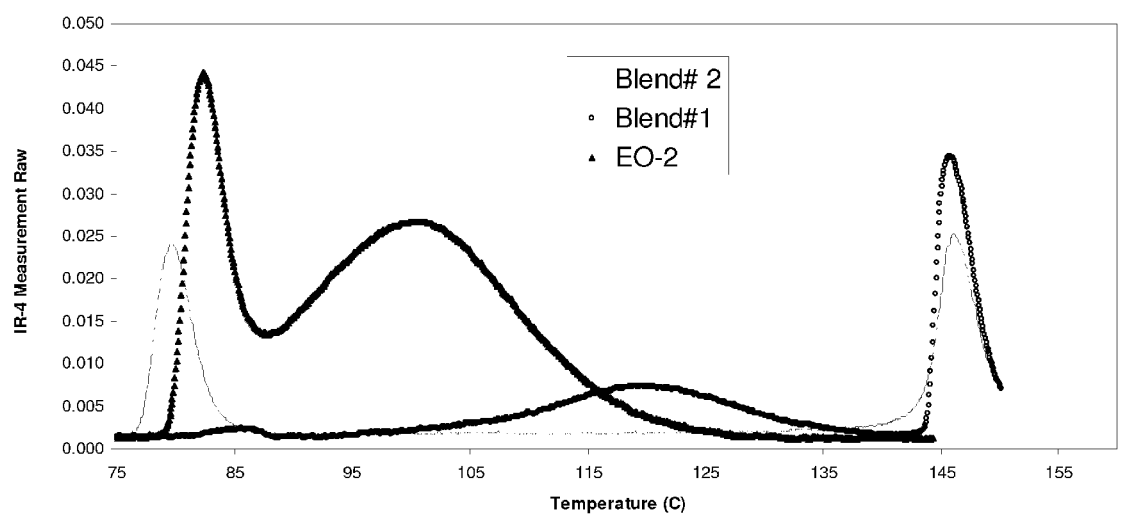
Figure 3. TGIC chromatogram of EO-2, Blend #1 and Blend #2.

CHROMATOGRAPHY OF POLYOLEFIN POLYMERS

BACKGROUND OF THE INVENTION

The disclosed invention is in the field of liquid chromatography. Liquid chromatography is used by the art to analyze polymers with regard to molecular size by Size Exclusion Chromatography (SEC) and with regard to chemical composition by High Performance Liquid Chromatography (HPLC). This disclosure relates to HPLC analysis of polymers with regard to chemical composition.

Polyolefin polymers (such as polymers and copolymers comprising polymerized ethylene monomer and/or propylene monomer) have long been analyzed with regard to chemical composition distribution by temperature rising elution fractionation (TREF) and crystallization analysis fractionation (CRYSTAF). However, neither TREF nor CRYSTAF can be used to analyze amorphous polyolefin polymers. Furthermore, both TREF and CRYSTAF require a relatively long analysis time. Therefore, the art turned to HPLC in an attempt to reduce analysis time and to expand the scope of analysis to amorphous polymers. Macko et al. apparently were the first to do so in 2003 by studying the retention of polyethylene standards on silica and zeolite stationary phases (J. Chrom. A, 1002 (2003) 55). Wang, et al. studied the retention of polyethylene and polypropylene by zeolites in 2005 (Macromolecules, V. 38, No. 25 (2005) 10341). Heinz and Pasch used a silica stationary phase to analyze polyethylene-polypropylene blends by HPLC (Polymer 46 (2005) 12040). Albrecht, et al., used a silica stationary phase to analyze ethylene-vinyl acetate copolymers by HPLC (Macromolecules 2007, 40, 5545). Albrecht, et al., used a silica stationary phase to analyze ethylene-propylene copolymers by HPLC (Macromol. Symp. 2007, 257, 46). A remaining problem for the HPLC analysis of polyolefin polymers is the limited separation efficiency obtained by the prior art methods.

SUMMARY OF THE INVENTION

In one embodiment, the invention is a method for multi-dimensional chromatography of a polyolefin polymer, comprising introducing a solution of the polyolefin polymer into a liquid flowing through a first liquid chromatography stationary phase or a field flow fractionation device and subsequently flowing the solution through a second liquid chromatography stationary phase, the second liquid chromatography stationary phase comprising graphitic carbon, the polyolefin polymer emerging from the liquid chromatography stationary phase with a retention factor greater than zero, preferably wherein the solution introduced into the first or second, or both, liquid chromatography stationary phase(s) is subjected to a temperature gradient.

Also preferably, the solution introduced into the first or second, or both, liquid chromatography stationary phase(s) can be subjected to a solvent gradient. The solution introduced into the first or second, or both, liquid chromatography stationary phase(s) can also be subjected to both a temperature and a solvent gradient. Preferably the polyolefin polymer is a copolymer consisting essentially of ethylene and an alpha-olefin, especially where the alpha-olefin consists essentially of 1-octene, or where the polyolefin polymer is a copolymer consisting essentially of propylene and an alpha-olefin. Also preferred is where the alpha-olefin consists essentially of ethylene. Desirably, the polyolefin polymer has a concentration in the solution of polyolefin polymer of greater than 0.1 milligrams per milliliter of solution.

The second liquid chromatography stationary phase preferably consists essentially of graphitic carbon. The first liquid chromatography stationary phase can also consist essentially of a GPC column or the second liquid chromatography stationary phase consists essentially of a GPC column.

Alternatively, the first liquid chromatography stationary phase can consist essentially of graphitic carbon.

In another embodiment, the invention is a method for one-dimensional chromatography of a polyolefin polymer, comprising introducing a solution of the polyolefin polymer into a liquid flowing through a liquid chromatography stationary phase, the liquid chromatography stationary phase comprising graphitic carbon, the polyolefin polymer emerging from the liquid chromatography stationary phase with a retention factor greater than zero, preferably, wherein the solution introduced into the liquid chromatography stationary phase is subjected to a temperature gradient, also preferably, wherein the solution introduced into the liquid chromatography stationary phase is subjected to a solvent gradient, or, wherein the solution introduced into the liquid chromatography stationary phase is subjected to both a temperature and a solvent gradient.

BRIEF DESCRIPTION OF THE DRAWINGS

FIG. 1a is a TGIC chromatogram of a metallocene polymerized ethylene-octene polymer;

FIG. 1b is a plot of Octene mol % in the fraction collected from TGIC of a metallocene polymerized ethylene-octene polymer;

FIG. 2 shows a calculation of octene mol % from 1H NMR determined by assuming the end group effect is negligible.

FIG. 3 is an overlay of TGIC chromatograms of polymers of EO-2, Blend #1 and Blend #2 using a graphitic carbon stationary phase.

DETAILED DESCRIPTION

This disclosure is a method for chromatography of a polyolefin polymer, comprising the step of: introducing a solution of the polyolefin polymer into a liquid flowing through a liquid chromatography stationary phase, the liquid chromatography stationary phase comprising graphitic carbon, the polyolefin polymer emerging from the liquid chromatography stationary phase with a retention factor greater than zero. The improvement of this disclosure centers on the use of a liquid chromatography stationary phase comprising graphitic carbon.

This disclosure is also a method for determining the monomer to comonomer ratio of a copolymer consisting essentially of ethylene or propylene and an alpha olefin comonomer, comprising the steps of: (a) flowing a liquid mobile phase into contact with a liquid chromatography stationary phase comprising graphitic carbon to produce an effluent stream of liquid mobile phase from the stationary phase; (b) introducing a solution of the copolymer into the liquid mobile phase so that the copolymer emerges in the effluent stream with a retention factor that varies as a mathematical function of the monomer to comonomer ratio of the copolymer.

The term "polyolefin polymer" in this disclosure is defined as all polymers and copolymers (including high pressure low density polyethylene (LDPE), heterogeneous polymers, random, block, and graft polymers, interpolymers and copolymers) comprising one or more polymerized monomers selected from the group consisting of ethylene, an alpha olefin having from 3-20 carbon atoms (such as 1-propylene, 1-butene, 1-hexene, 1-heptene and 1-octene), 4-methyl-1-pentene, and/or acetylenically unsaturated monomers having from 2-20 carbons, and/or diolefins having from 4-18 carbons and any other monomer used in the art to modify the density of a polymer. Heterogeneous polymers include Ziegler-Natta polymerized polymers such as LLDPE and HDPE and include products such as DOWLEX™ Linear Low Density Polyethylene (LLDPE) made by The Dow Chemical Company. The random copolymers include those polymerized using metallocene or constrained geometry catalyst technology and include polymers such as AFFINITY™ Polyolefin Plastomer and ENGAGE™ Polyolefin Elastomer both available from The Dow Chemical Company, and EXACT™ Polyolefin available from Exxon-Mobil. Methods for polymerizing these random copolymers are well known in the art and include those described in U.S. Pat. Nos. 5,272,236 and 5,278,272. The block copolymers include those polymerized using chain shuttling technology and two catalyst species, such as is disclosed in U.S. Pat. No. 7,355,089, and include polymers such as INFUSE™ Olefin Block Copolymers made by The Dow Chemical Company. In addition the term "polyolefin polymer" in this disclosure is defined as a polymer having an average molecular weight, as determined by light scattering, greater than 1,000 grams per mole (preferably greater than 2,000 grams per mole and more preferably greater than 4,000 grams per mole and can be as high as 10 million grams per mole). The polyolefin polymer can be a copolymer consisting essentially of polymerized ethylene monomer and a polymerized alpha olefin monomer such as 1-octene. The polyolefin polymer can be a copolymer consisting essentially of polymerized propylene monomer and a polymerized alpha olefin monomer such as ethylene. Such propylene based polymers include homopolymer polypropylene, impact propylene based copolymers, and random propylene based copolymers. Other more specialized polymers also benefit from the method and apparatus disclosed herein and include ethylene/acrylic acid copolymers, ethylene/vinyl acetate copolymers and ethylene/styrene interpolymers, halogenated polymers, and polymers containing maleic anhydride moeities.

In most applications the temperature of the solution of the polyolefin polymer, the temperature of the liquid chromatography stationary phase and the temperature of the detector will be controlled at an elevated temperature to increase the solubility of the polyolefin polymer, e.g., to render the polyolefin polymer soluble. The concentration of the polyolefin polymer in the solution of polyolefin polymer is preferably greater than 0.1 milligrams per milliliter of solution, especially greater than 2 mg/mL. The solvent used for the solution of the polyolefin polymer is preferably decanol when the polyolefin polymer is polyethylene or polypropylene. Any suitable liquid mobile phase can be used in the method of this disclosure. A temperature gradient mobile phase is preferred in the method of this disclosure. The temperature of the liquid chromatography stationary phase can be increased during the method of this disclosure and/or the solvent composition can be a gradient during this method. A mobile phase having no aliphatic hydrogen content (such as 1,2,4-trichlorobenzene) facilitates the use of an infrared detector for the method of this disclosure.

Any liquid chromatography stationary phase that comprises graphitic carbon can be used in the method of this disclosure. The term "graphitic carbon" in this disclosure is defined as all varieties of materials comprising the element carbon in the allotropic form of graphite irrespective of the presence of structural defects if the three-dimensional hexagonal crystalline long-range order of graphite can be detected in the material by diffraction methods (such as X-ray diffraction spectroscopy) independent of the volume fraction and the homogeneity of distribution of such crystalline domains. Carbon nanotubes and carbon "buckeyballs" are examples of forms of graphitic carbon that are useful in the method of this disclosure. Preferably, the liquid chromatography stationary phase consists essentially of graphitic carbon, especially porous graphitic carbon. The graphitic carbon is usually packed into columns and comprises flat sheets of hexagonally arranged carbon atoms at the molecular level. The graphitic carbon desirably has a particle size of from about 1 to about 10 microns, preferably an average particle size of about 3 microns, or 5 microns or 7 microns, and preferably has an average pore size of about 200 to about 300 Angstroms, more preferably an average pore size of about 250 Angstroms. The internal surface of the graphitic carbon has an area of about 100 to about 140 square meters/gram, preferably about 120 square meters/gram. The length of the columns is typically from about 30 mm to about 100 mm and can have a diameter of from about 2 mm to about 5 mm. An example of a commercially available liquid chromatography stationary phase that consists essentially of graphitic carbon is believed to include the HYPERCARB brand HPLC column from Thermo Scientific, Waltham Mass. An example of a commercially available liquid chromatography stationary phase that comprises graphitic carbon is believed to include the DISCOVERY ZR-CARBON brand HPLC column from Sigma Aldrich, St. Louis, Mo. Leboda, et al, Materials Chemistry and Physics 55 (1998) pages 1-29, is a literature review of HPLC carbon adsorbents.

The method of this disclosure can be coupled, on or off line, with other analytical methods. For example, the effluent from an SEC column containing an ethylene 1-octene polyolefin copolymer of a selected molecular size can be analyzed by the method of this disclosure to determine the ratio of ethylene to 1-octene of the copolymer of the selected molecular size.

The method of this disclosure could be scaled up to include large scale fractionations of many grams or many pounds of polymer by scaling up the size of the apparatus and the graphitic column.

This disclosure could include a temperature gradient in addition to and/or a solvent gradient as a way to perform the fractionation.

In addition this disclosure could include a fractionation in a commercial process to refine the purity of the comonomer distribution of the commercial product.

The crystallization elution fractionation (CEF) technique relies upon dynamic crystallization of polymer from a moving carrier. The crystallization substrate is normally spherical glass beads or perhaps stainless steel shot, and is more or less inert with respect to physical interaction with the polymer. A modification of the technique substitutes a more interactive substrate, in this case a carbon surface in a commercial column known as "Hypercarb" potentially possible packing materials of carbon nanotubes or silicon nanotubes for surface area and surface property, and does not rely upon dynamic crystallization of the polymer. In other words, adsorption to the carbon surface at a fixed temperature has replaced dynamic crystallization. The new technique is known as thermal gradient interaction chromatography (TGIC). Both CEF and TGIC rely upon a thermal gradient to elute polymer.

In order to investigate the mechanism of separation more fully, material is collected from the TGIC column for the purpose of further analysis and identification. Because the column eluent is relatively dilute with respect to the concentrations needed by instrumental techniques used for identification, such as NMR, it is necessary to make multiple injections, and collect and combine respective fractions.

Experimental

Example 1 of the thermal gradient interaction chromatography. A metallocene polymerized ethylene-octene copolymer product (EO-1) is chosen for fractionation. EO-1 has a melt index of 0.82 g/10 minutes and a density of 0.885 g/cm$^3$; the sample for use in TGIC is prepared by weighing approximately 32 mg of polymer into a 10 ml GC glass vial, which is capped and placed in Crystallization Elution Fractionation (CEF) (PolymerChar, Spain) auto sampler. The instrument adds o-dichlorobenzene (ODCB), containing 300 ppm butylated hydroxytoluene (BHT) as an oxidation inhibitor, to the vial, producing a solution that is approximately 4 mg/mL in polymer. The dissolution is done by the autosampler at 160° C. for 90 minutes. The CEF is equipped with an IR-4 detector operating at 150° C. The delay volume (the volume that the first polymer fraction has to travel before reaching the detector) is 1.5 ml.

The column is a 10 cm long HYPERCARB column, part number 35005-104646, and the mobile phase is ODCB. The injection volume is 300 μL, and the injection temperature is 150° C. The polymer solution is loaded onto the column at 110° C. The polymer solution is kept at 110° C. for 2 minutes, and then cooled down to 90° C. at 10° C./min, and kept at 90° C. for 2 minutes for thermal equilibrium. No solvent flow is used during the cooling and thermal equilibrium steps. Polymer solution is eluted from 90° C. to 165° C. at 3° C./min at a flow rate of 0.7 ml/min. The chromatogram is shown in FIG. 1a.

Fraction collection is performed using a Spectra Chrom CF-1 fraction collector. The collector is operated in timed mode, changing collection vials every 2 minutes (every 6° C.). The vials are glass. A separate solvent line is used to connect the column directly to the fraction collector diverter valve. The CEF detector is bypassed. The collection is started manually each time at the moment when the temperature program and pump flow of the elution process are initiated. The same vials are used for each injection, so that the timed fractions are accumulated. A total of 12 fractions are collected from 90 to 165° C.

After 11 injections are completed, the twelve vials are capped with aluminum foil and placed in a vacuum oven at 140° C. to remove the ODCB. The evaporation of the solvent left a thin layer of polymer on the sides and bottom of the vials. The vials of fraction #1, 2, 3, 4, 5, 6, 7, 8 and 12 are submitted for $^1$H NMR analysis.

The experimental conditions for $^1$H NMR analysis are: 1.4 g of tetrachloroethane-d$_2$ containing 0.001 M Cr(AcAc)$_3$ is added to the vial which contains the polymer. The solution is heated to 120° C. to wash off the polymer. The solution is transferred to a 10 mm NMR tube. The procedure is repeated twice. $^1$H NMR is acquired with a 10 mm cryoprobe on a Bruker AV400 at 120° C. The residual water signal is very close to the signals from methine and methylene. In order to measure the octene content accurately, a new method which reduces the effect of residual water is developed. The method uses 3 drops of DMSO-d$_6$ to move the water signal down field to get relatively accurate signal integrals of methine and methylene. Two proton NMR spectra were acquired to get the octene content. The first is a regular $^1$H NMR, the signal integral from methine and methylene is obtained after setting the integral of residual signal from TCE-d$_2$ to 100. The second is a $^1$H NMR with slight presaturation of the signal of methine and methylene to get more accurate integral of methyl relative to residual signal from TCE-d$_2$ which is set to 100 again. Octene content is calculated according to FIG. 2.

The plot of the comonomer mol % of each fraction is plotted against the starting temperature of each fraction (FIG. 1b).

Example 2: the thermal gradient interaction chromatography on polymerized ethylene-octene (EO) polymers and blends. EO-2 has a melt index of 1 g/10 minutes and a density of 0.865 g/cm$^3$. EO-3 has a melt index of 66 g/10 minutes and a density of 0.882 g/cm$^3$. Blend #1 is 50:50 (wt/wt) solution blend of a high density homopolymer polyethylene at melt index of 1 g/10 min and density of 0.953 g/cm$^3$, and EO-3. Blend #2 is a 50:50 (wt/wt) solution blend of isotactic polypropylene at MFR (ASTM D 1238 condition 2.16 kg/230° C.) of 13 g/10 minutes and NIST SRM linear polyethylene 1484a.

The dissolution time is 120 minutes. The polymer solutions are loaded onto the column at 100° C. The polymer solution is kept at 100° C. for 2 minutes, and then cooled down to 80° C. at 20° C./min, and kept at 80° C. for 5 minutes for thermal equilibrium, Polymer solution is eluted from 80° C. to 165° C. at 4° C./min at a flow rate of 0.5 ml/min. Other experimental conditions are the same as Example 1. The chromatogram for EO-2, Blend #1 and #2 are shown in FIG. 3.

To summarize, FIG. 1b shows the composition based separation of EO-1, which shows the comonomer content from 0 to at least 20 mole percent using the invention, whereas using prior art techniques such as temperature rising elution fractionation (TREF) and crystallization fractionation (CRYSTAF), such separation on a wide range of comonomer content is not possible. Further, use of TGIC offers a fraction of the otherwise required analysis time for TREF or CRYSTAF. Also since the fractionation mechanism is different from TREF and CRYSTAF (both based on crystallization ability), use of TGIC allows separation based on comonomer only, not cocrystallization effects. Since there is no solvent gradient, this opens a wide window of detectors for TGIC, such as commercially available light scattering detectors, viscometers and the IR-5 detector (PolymerChar).

FIG. 3 shows an improved resolution for polyolefin polymers with different composition. For example, for Blend #2, the separation between isotactic polypropylene and HDPE is at least 60° C., while ATREF would provide ~20° C. separation, CRYSTAF would have only less than 10° C. separation.

What is claimed is:

1. A method for multi-dimensional chromatography of a polyolefin polymer, comprising introducing a solution of the polyolefin polymer into a liquid flowing through a first liquid chromatography stationary phase or a field flow fractionation device and subsequently flowing the solution through a second liquid chromatography stationary phase, the second liquid chromatography stationary phase comprising graphitic carbon, the polyolefin polymer emerging from the liquid chromatography stationary phase with a retention factor greater than zero.

2. The method of claim 1, wherein the solution introduced into the first or second, or both, liquid chromatography stationary phase(s) is subjected to a temperature gradient.

3. The method of claim 1, wherein the solution introduced into the first or second, or both, liquid chromatography stationary phase(s) is subjected to a solvent gradient.

4. The method of claim 1, wherein the solution introduced into the first or second, or both, liquid chromatography stationary phase(s) is subjected to both a temperature gradient and a solvent gradient.

5. The method of claim 1, where the polyolefin polymer is a copolymer consisting essentially of ethylene and an alpha-olefin.

6. The method of claim 5, where the alpha-olefin consists essentially of 1-octene.

7. The method of claim 1, where the polyolefin polymer is a copolymer consisting essentially of propylene and an alpha-olefin.

8. The method of claim 7, where the alpha-olefin consists essentially of ethylene.

9. The method of claim 1, where the polyolefin polymer has a concentration in the solution of polyolefin polymer of greater than 0.1 milligrams per milliliter of solution.

10. The method of claim 1, where the second liquid chromatography stationary phase consists essentially of graphitic carbon.

11. The method of claim 1, where the first liquid chromatography stationary phase consists essentially of a GPC column.

12. The method of claim 1, where the second liquid chromatography stationary phase consists essentially of a GPC column.

13. The method of claim 12 wherein the first liquid chromatography stationary phase consists essentially of graphitic carbon.

14. A method for one-dimensional chromatography of a polyolefin polymer, comprising introducing a solution of the polyolefin polymer into a liquid flowing through a liquid chromatography stationary phase, the liquid chromatography stationary phase comprising graphitic carbon, the polyolefin polymer emerging from the liquid chromatography stationary phase with a retention factor greater than zero, and
   wherein the solution introduced into the liquid chromatography stationary phase is subjected to a temperature gradient.

15. The method of claim 14, wherein the solution introduced into the liquid chromatography stationary phase is subjected to a solvent gradient.

* * * * *